United States Patent [19]

Wright et al.

[11] 4,115,405

[45] Sep. 19, 1978

[54] 6-NITRO-OR AMINO-4-CHROMANONE OXIME

[75] Inventors: George C. Wright; Marvin M. Goldenberg, both of Norwich, N.Y.

[73] Assignee: Morton-Norwich Products, Inc., Norwich, N.Y.

[21] Appl. No.: 812,107

[22] Filed: Jul. 1, 1977

[51] Int. Cl.$^2$ .................. C07D 311/02; A61K 31/35
[52] U.S. Cl. ................................. 260/345.2; 424/283
[58] Field of Search ...................................... 260/345.2

[56] References Cited

PUBLICATIONS

Huckle et al., J. Med. Chem., 12, 277 (1969).

*Primary Examiner*—Nicky Chan
*Attorney, Agent, or Firm*—Anthony J. Franze

[57] ABSTRACT

The compounds 6-nitro- or amino-4-chromanone oxime are useful as anti-inflammatory agents.

1 Claim, No Drawings

6-NITRO-OR AMINO-4-CHROMANONE OXIME

This invention is concerned with compounds of the formula:

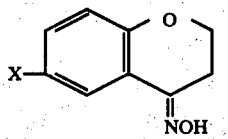

wherein X is nitro or amino.

These compounds possess pharmacological activity. They are particularly effective as anti-inflammatory agents as evidenced by their ability to combat edema induced in rats by the administration of carrageenin. Thus, when administered at a dose of 300 mg/kg suspended in a vehicle such as aqueous methylcellulose to rats receiving carrageenin, edema associated with that substance is inhibited (Winter el al. P.S.E. B.M. 114:544 (1962)).

These compounds are readily compounded in suitable pharmaceutical formulations such as elixirs, tablets, capsules, suspensions and the like using commonly employed excipients and adjuvants with which there is no incompatibility.

In order that this invention may be readily available to and understood by those skilled in the art, the following examples present the currently preferred procedure for the preparation thereof.

EXAMPLE I

6-Nitro-4-chromanone Oxime

A solution of 79 g (1.14 mole) of hydroxylamine hydrochloride in 770 ml of $H_2O$, contained in a 2 l. Erlenmeyer flask, was treated with 619 ml of 10% NaOH, 150 g (0.78 mole) of 6-nitro-4-chromanone and enough ethanol (750 ml) to produce a solution at the boiling point. The reaction mixture was boiled for 25 min., cooled to 50° over 2 hrs., and filtered. The filtrate was refrigerated overnight and filtered. The tan crystalline solid was washed with 200 ml of ethanol and dried, m.p. 173°–178°. Yield: 60 g (37%).

The product was recrystallized from 2.4 l. of benzene (Darco), cooled overnight at 10%, washed with 240 ml of benzene and dried, m.p. 185°–186°. Yield: 44 g (27%).

Anal. Calcd. For $C_9H_8N_2O_4$: C, 51.92; H, 3.87; N, 13.46. Found C, 51.92; H, 3.79; N, 13.34.

EXAMPLE II

6-Amino-4-chromanone Oxime

A 21 g (0.10 mole) portion of the compound of Example I, 380 ml of ethanol, and 3 g of 5% Pd/C (50% $H_2O$) were placed in a 1 l. pressure bottle and subjected to hydrogenation at 49 psig. The hydrogen uptake was 24 lbs. (Theory: 24 lbs. at 26°) in 14 min. The reduction mixture was filtered, cooled and filtered. The crystalline solid was washed with 40 ml of ethanol and dried, m.p. 160°–163°. Yield: 9 g (50%).

The product was recrystallized from 142 ml of ethanol, Darco, Washed with 20 ml of ethanol and dried, m.p. 164°–165°. Yield: 5 g (28%).

Anal. Calcd. for $C_9H_{10}N_2O_2$: C, 60.66; H, 5.66; N, 15.72. Found: C, 60.33; H, 5.83; N, 15.34.

What is claimed is:

1. The compound 6-amino-4-chromanone oxime.